(12) United States Patent
Matsushima et al.

(10) Patent No.: US 9,119,746 B2
(45) Date of Patent: Sep. 1, 2015

(54) ABSORBENT ARTICLE AND METHOD OF PRODUCING ABSORBENT ARTICLE

(75) Inventors: Azusa Matsushima, Kagawa (JP); Kouichi Yamaki, Kagawa (JP)

(73) Assignee: Unicharm Corporation, Ehime (JP)

( * ) Notice: Subject to any disclaimer, the term of this patent is extended or adjusted under 35 U.S.C. 154(b) by 245 days.

(21) Appl. No.: 13/876,544

(22) PCT Filed: Sep. 28, 2011

(86) PCT No.: PCT/JP2011/072901
§ 371 (c)(1),
(2), (4) Date: Mar. 28, 2013

(87) PCT Pub. No.: WO2012/043862
PCT Pub. Date: Apr. 5, 2012

(65) Prior Publication Data
US 2013/0184664 A1    Jul. 18, 2013

(30) Foreign Application Priority Data
Sep. 29, 2010   (JP) .................................. 2010-219978

(51) Int. Cl.
*A61F 13/15*      (2006.01)
*A61F 13/56*      (2006.01)
*A61F 13/511*     (2006.01)
(Continued)

(52) U.S. Cl.
CPC ..... *A61F 13/15211* (2013.01); *A61F 13/15707* (2013.01); *A61F 13/511* (2013.01); *A61F 13/51476* (2013.01); *A61F 13/5611* (2013.01); A61F 2013/15235 (2013.01); A61F 2013/5149 (2013.01); A61F 2013/51078 (2013.01); Y10T 156/1002 (2015.01); Y10T 156/1043 (2015.01)

(58) Field of Classification Search
CPC .............. A61F 13/15211; A61F 13/47; A61F 13/4704; A61F 13/5611; A61F 13/51476; A61F 2013/15235; A61F 2013/51078; A61F 2013/5108; A61F 2013/51083; A61F 2013/51085; A61F 2013/51088; A61F 2013/51488; A61F 2013/5149
See application file for complete search history.

(56) References Cited

U.S. PATENT DOCUMENTS

| | | | | |
|---|---|---|---|---|
| 4,376,440 A | * | 3/1983 | Whitehead et al. | 604/387 |
| 4,959,265 A | * | 9/1990 | Wood et al. | 428/343 |
| 5,607,415 A | * | 3/1997 | Datta et al. | 604/385.21 |

(Continued)

FOREIGN PATENT DOCUMENTS

| | | |
|---|---|---|
| JP | 2001-145669 A | 5/2001 |
| JP | 2001/145669 A | 5/2001 |

(Continued)

OTHER PUBLICATIONS

International Search Report from corresponding PCT application No. PCT/JP2011/072901 dated Dec. 13, 2011 (4 pgs).

*Primary Examiner* — Lynne Anderson
(74) *Attorney, Agent, or Firm* — Brinks Gilson & Lione

(57) ABSTRACT

An absorbent article having water disintegratability that includes a water disintegratable top sheet, a water disintegratable back sheet, a pressure-sensitive adhesive section for attaching the absorbent article to clothing, disposed on the surface of the back sheet opposite the top sheet, and a release sheet for protection of a contact surface of the pressure-sensitive adhesive section which contacts with clothing. One or more protrusions and one or more depressions are formed on the contact surface of the pressure-sensitive adhesive section.

12 Claims, 5 Drawing Sheets

(51) Int. Cl.
  *A61F 13/514* (2006.01)
  *A61F 13/51* (2006.01)

(56) References Cited

U.S. PATENT DOCUMENTS 5,674,341 A * 10/1997 Ng .............................. 156/234
6,432,095 B1    8/2002 Wada et al.
6,500,159 B1 * 12/2002 Carvalho ................ 604/385.01
2002/0058919 A1 5/2002 Hamilton et al.
2011/0144607 A1 6/2011 Suzuki et al.
2011/0184363 A1 * 7/2011 Suzuki et al. ................ 604/364
2012/0271268 A1 * 10/2012 Suzuki et al. .......... 604/385.101
2013/0035656 A1 * 2/2013 Moriya et al. ................ 604/380

FOREIGN PATENT DOCUMENTS

| JP | 2003-506151 A | 2/2003 |
| JP | 2006-055268 A | 3/2006 |
| JP | 2007-135660 A | 6/2007 |
| JP | 2009-268537 A | 11/2009 |

* cited by examiner (a)

(b)

(a)

(b)

(c)

ABSORBENT ARTICLE AND METHOD OF PRODUCING ABSORBENT ARTICLE

RELATED APPLICATION

This application is a 35 U.S.C. §371 national phase filing of International Patent Application No. PCT/JP2011/072901, filed Sep. 28, 2011, through which and to which priority is claimed under 35 U.S.C. §119 to Japanese Patent Application No. 2010-219978, filed Sep. 29, 2010.

TECHNICAL FIELD

The present disclosure relates to an absorbent article wherein the pressure-sensitive adhesive section have a specific contact surface, and to a method for producing the absorbent article.

BACKGROUND ART

Absorbent articles with water disintegratability, such as water disintegratable sanitary napkins, panty liners and urine-absorbing pads, have been developed and are marketed. Such absorbent articles are composed of water disintegratable materials, and when flushed through large amounts of water, such as in a flush toilet, they disperse in the water.

Such absorbent articles usually include on the back sheet a pressure-sensitive adhesive section to attach the absorbent article to clothing, such as underwear, and often have a flat pressure-sensitive adhesive section coated on a flat back sheet. Therefore, when the unused absorbent article from which the release sheet has been released is accidentally discarded in a flush toilet, the entire surface of the pressure-sensitive adhesive section sometimes clings to the toilet bowl and is difficult to peel off. In addition, if it is flushed without clinging to the toilet bowl, it can cling to the inner walls of the sewage pipes, causing clogging of pipes.

In order to solve this problem, PTL 1, for example, discloses a water disintegratable absorbent article having, on the back side of a back sheet, pressure-sensitive adhesive sections provided at a plurality of locations at spacings in the longitudinal direction and the transverse direction of the absorbent article, to affix the absorbent article to an exterior attachment surface, wherein the spacing between adjacent pressure-sensitive adhesive sections is longer than the maximum fiber length of the fibers in the back sheet. FIG. 4 of PTL 1 discloses an absorbent article in which a plurality of dot-like pressure-sensitive adhesive sections are configured in a zigzag fashion.

PTL 2 describes an absorbent article that includes an adhesive system comprising a plurality of three-dimensional protruding sections that are deformable essentially in a two-dimensional architecture, and an interconnected network structure of an adhesive surrounding the protruding sections, which prevents inadvertent contact of the three-dimensional protruding sections with the outer walls until it deforms essentially in a two-dimensional architecture. With the absorbent article described in PTL 2, the adhesive surface is protected by the three-dimensional protruding sections, and therefore even if it is accidentally flushed into a flush toilet before wear, there is a low chance of it clinging to the toilet bowl or inner walls of the pipes.

CITATION LIST

Patent literature

PTL 1 Japanese Unexamined Patent Publication No. 2001-145669
PTL 2 Japanese Unexamined Patent Publication No. 2003-506151

SUMMARY OF INVENTION

Technical Problem

With the absorbent article described in PTL 1, however, even though the low total area of the pressure-sensitive adhesive sections lowers the chance of clinging to the toilet bowl and inner walls of pipes and can be easily released even after it has temporarily attached to the toilet bowl or inner walls of pipes, the attaching force of the absorbent article to clothing is also low, such that the absorbent article can shift or slip from clothing during wear. In addition, since a plurality of pressure-sensitive adhesive sections, each with a small area, are disposed on the back sheet in the absorbent article described in PTL 1, the edge lengths of the pressure-sensitive adhesive sections increase, and this can tend to cause adhesive residue in which some of the pressure-sensitive adhesive sections remain on clothing.

Also, since the absorbent article described in PTL 2 has the adhesive surface protected by the three-dimensional protruding sections, it is not possible to achieve temporary positioning on clothing, such as underwear during wear, and therefore fitting becomes more difficult. Furthermore, the absorbent article described in PTL 2 has a complex structure and is costly.

It is therefore an object of the present disclosure to provide an absorbent article that can provide both a release property for temporary positioning, and an attaching property during wear.

Solution to Problem

As a result of diligent research directed toward solving the problems described above, the present inventors have found an absorbent article having water disintegratability comprising: a water disintegratable top sheet, a water disintegratable back sheet, a pressure-sensitive adhesive section for attaching the absorbent article to clothing, disposed on the surface of the back sheet opposite the top sheet, and a release sheet for protection of a contact surface of the pressure-sensitive adhesive section which contacts with clothing, wherein one or more protrusions and one or more depressions are formed on the contact surface of the pressure-sensitive adhesive section.

Specifically, the present disclosure relates to the following aspects.

[Aspect 1]

An absorbent article having water disintegratability comprising:
  a water disintegratable top sheet,
  a water disintegratable back sheet,
  a pressure-sensitive adhesive section for attaching the absorbent article to clothing, disposed on the surface of the back sheet opposite the top sheet, and
  a release sheet for protection of a contact surface of the pressure-sensitive adhesive section which contacts with clothing,
  wherein one or more protrusions and one or more depressions are formed on the contact surface of the pressure-sensitive adhesive section.

[Aspect 2]

The absorbent article according to aspect 1, wherein the back sheet has one or more protruding sections and one or more depressed sections, and the protrusions and depressions of the pressure-sensitive adhesive section are formed along the protruding sections and depressed sections, respectively.

[Aspect 3]

The absorbent article according to aspect 2, wherein the back sheet comprises a plurality of mutually independent protruding sections and a continuous depressed section surrounding the protruding sections.

[Aspect 4]

The absorbent article according to aspect 3, wherein the protruding sections of the back sheet are configured in a zigzag fashion.

[Aspect 5]

The absorbent article according to any one of aspects 2 to 4, wherein the pressure-sensitive adhesive section comprises a plurality of mutually independent regions, and the protrusions and depressions are formed in each of the regions.

[Aspect 6]

The absorbent article according to aspect 5, wherein the back sheet comprises a water disintegratable nonwoven fabric or a water disintegratable sheet, and the water disintegratable nonwoven fabric or water disintegratable sheet is present on the surface of the back sheet that contacts with the pressure-sensitive adhesive section.

[Aspect 7]

The absorbent article according to aspect 5 or 6, wherein the area of each of the regions of the pressure-sensitive adhesive section is larger than the area of each of the protruding sections of the back sheet.

[Aspect 8]

The absorbent article according to any one of aspects 5 to 7, wherein a length of each of the regions of the pressure-sensitive adhesive section in a lengthwise direction of the absorbent article is longer than a length in the direction perpendicular to a lengthwise direction of the absorbent article.

[Aspect 9]

The absorbent article according to aspect 6, wherein a spacing between the regions of the pressure-sensitive adhesive section is longer than fiber lengths of fibers composing the water disintegratable nonwoven fabric or water disintegratable sheet.

[Aspect 10]

The absorbent article according to any one of aspects 1 to 9, wherein the protrusions and depressions are formed on the contact surface of the pressure-sensitive adhesive section by integrally shaping the back sheet, the pressure-sensitive adhesive section and the release sheet.

[Aspect 11]

The absorbent article according to any one of aspects 1 to 9, wherein the protrusions and depressions are formed on the contact surface of the pressure-sensitive adhesive section by integrally shaping the top sheet, back sheet, the pressure-sensitive adhesive section and the release sheet.

[Aspect 12]

An absorbent article having water disintegratability comprising:

a water disintegratable top sheet, a water disintegratable back sheet, a pressure-sensitive adhesive section for attaching the absorbent article to clothing, disposed on the surface of the back sheet opposite the top sheet, and a release sheet for protection of a contact surface of the pressure-sensitive adhesive section which contacts with clothing, wherein the back sheet has a plurality of protruding sections configured in a zigzag fashion and a continuous depressed section surrounding the protruding sections, and one or more protrusions and one or more depressions are formed on the contact surface of the pressure-sensitive adhesive section, along the protruding sections and depressed sections, respectively, the pressure-sensitive adhesive section comprises a plurality of mutually independent regions, and the protrusions and depressions are formed in each of the regions, the back sheet comprises a water disintegratable nonwoven fabric or water disintegratable sheet, the area of each of the regions of the pressure-sensitive adhesive section in which the water disintegratable nonwoven fabric or water disintegratable sheet is present, on the surface of the back sheet which contacts with the pressure-sensitive adhesive section, is larger than the area of each of the protruding sections of the back sheet, a length of each of the regions of the pressure-sensitive adhesive section in a lengthwise direction of the absorbent article is longer than its length in a direction perpendicular to the lengthwise direction of the absorbent article, and a spacing between the regions of the pressure-sensitive adhesive section is longer than fiber lengths of fibers composing the water disintegratable nonwoven fabric or water disintegratable sheet, and the protrusions and depressions are formed on the contact surface of the pressure-sensitive adhesive section by integrally shaping the top sheet, back sheet, pressure-sensitive adhesive section and release sheet.

[Aspect 13]

The absorbent article according to aspect 1, wherein the pressure-sensitive adhesive section has different thicknesses at the protrusions and depressions, whereby the protrusions and depressions are formed on the contact surface of the pressure-sensitive adhesive section.

[Aspect 14]

A method of producing an absorbent article having water disintegratability comprising a water disintegratable top sheet, a water disintegratable back sheet, a pressure-sensitive adhesive section for attaching the absorbent article to clothing, and a release sheet for protection of the contact surface of the pressure-sensitive adhesive section which contacts with clothing, comprising the steps of:

layering the back sheet, pressure-sensitive adhesive section and release sheet with the pressure-sensitive adhesive section inserted therebetween to form a layered structure, shaping the layered structure so that the contact surface of the pressure-sensitive adhesive section has unevenness, to form a shaped layered structure, and layering the top sheet on the shaped layered structure.

[Aspect 15]

A method of producing an absorbent article having water disintegratability comprising a water disintegratable top sheet, a water disintegratable back sheet, a pressure-sensitive adhesive section for attaching the absorbent article to an exterior attachment surface, and a release sheet for protection of the contact surface of the pressure-sensitive adhesive section which contacts with clothing, comprising the steps of:

layering the top sheet, the back sheet, the pressure-sensitive adhesive section and the release sheet with the pressure-sensitive adhesive section disposed between the back sheet and release sheet, to form a layered structure, and shaping the layered structure so that the contact surface of the pressure-sensitive adhesive section has unevenness.

Advantageous Effects of Invention

The absorbent article of the disclosure can provide both a release property for temporary positioning, and an attaching property during wear.

DESCRIPTION OF EMBODIMENTS

The absorbent article of the disclosure, and a method for producing the absorbent article, will now be explained in detail.

The absorbent article of the disclosure may be any one that has water disintegratability and becomes attached to clothing, without any particular restrictions, and this includes water disintegratable sanitary napkins, panty liners, urine-absorbing pads and the like.

Such clothing also includes underwear, such as briefs and panties.

Figure 1:
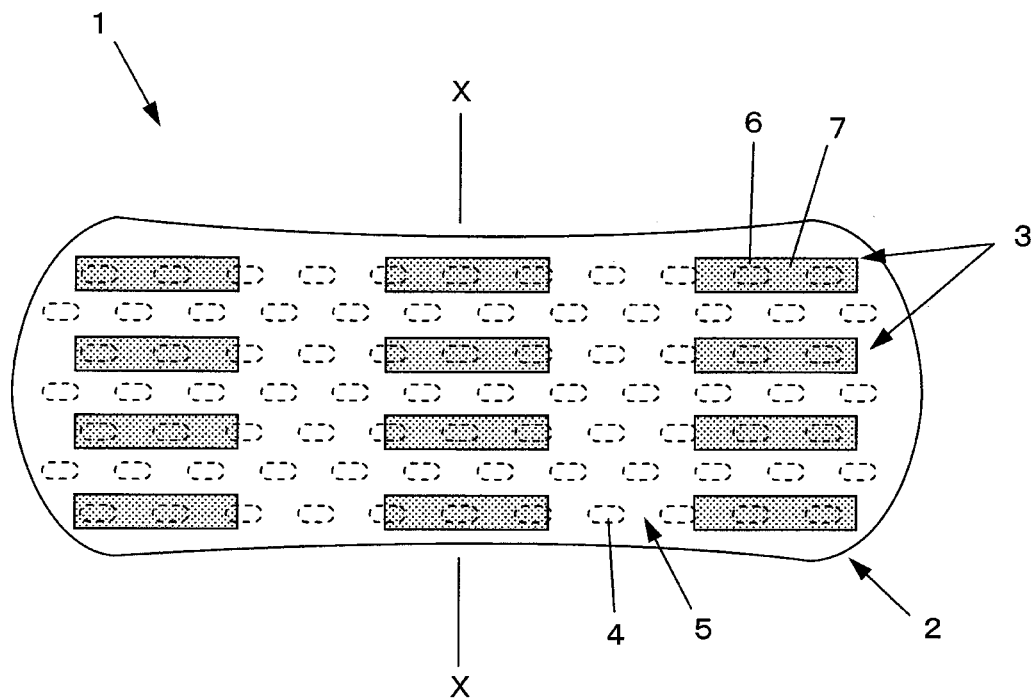
FIG. 1 is a diagram showing an embodiment of an absorbent article of the disclosure.

FIG. 1 is a diagram showing an embodiment of an absorbent article of the disclosure. FIG. 1 is a view from the back sheet side, with the release sheet removed. In FIG. 1, the left side is the front of the absorbent article, and the right side is the back of the absorbent article. The absorbent article 1 shown in FIG. 1 comprises a top sheet (not shown), a second sheet (not shown), a leakproof sheet (not shown), a back sheet 2 and pressure-sensitive adhesive section 3, there being formed in the back sheet 2 a plurality of protruding sections 4 and a continuous depressed section 5 surrounding the protruding sections 4.

In the absorbent article 1 shown in FIG. 1, the protruding sections 4 of the back sheet 2 are configured in a zigzag fashion.

Also, in the absorbent article 1 shown in FIG. 1, protrusions 6 and depressions 7 are formed in the pressure-sensitive adhesive section 3, along the protruding sections 4 and depressed sections 5 of the back sheet 2.

As shown in FIG. 1, the back sheet has protruding sections and depressed sections, with protrusions and depressions formed in the pressure-sensitive adhesive section along the protruding sections and depressed sections, and therefore since it is not necessary for the thickness of the pressure-sensitive adhesive section themselves to vary, it is possible to form large unevenness with smaller pressure-sensitive adhesive section, than when unevenness is formed by varying the thicknesses of the pressure-sensitive adhesive section.

Furthermore, in the absorbent article 1 shown in FIG. 1, the pressure-sensitive adhesive section 3 comprises a plurality of mutually independent regions, with protrusions 6 and depressions 7 formed in each region.

Also, in the absorbent article 1 shown in FIG. 1, the area of each region of the pressure-sensitive adhesive section 3 is larger than the area of any protruding section 4 of the back sheet 2.

Figure 2:
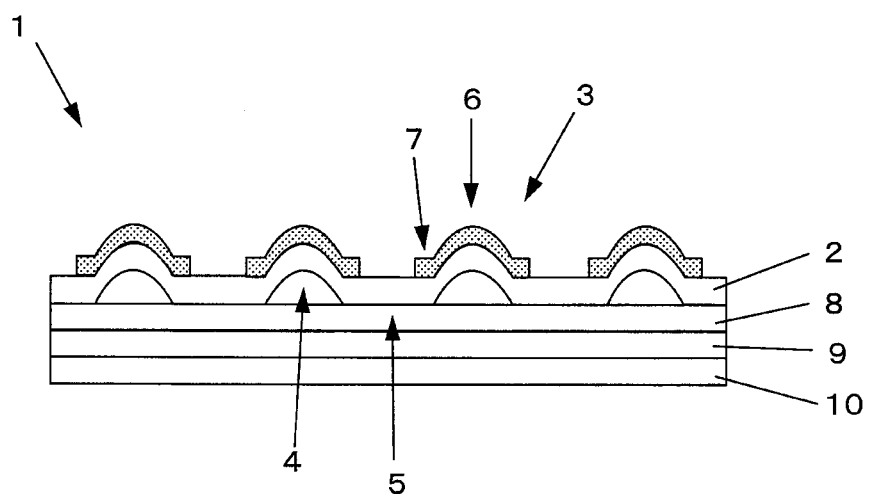
FIG. 2 is a view of the absorbent article shown in FIG. 1, along cross-section X-X.

FIG. 2 is a view of cross-section X-X of the absorbent article 1 shown in FIG. 1. The absorbent article 1 shown in FIG. 2 comprises a top sheet 10, a second sheet 9, a leakproof sheet 8, a back sheet 2 and pressure-sensitive adhesive section 3, each being bonded by a hot-melt adhesive. The back sheet 2 has protruding sections 4 and depressed sections 5, with protrusions 6 and depressions 7 being formed in the pressure-sensitive adhesive section 3 along the protruding sections 4 and depressed sections 5. The pressure-sensitive adhesive section 3 has an essentially uniform thickness.

Figure 3:
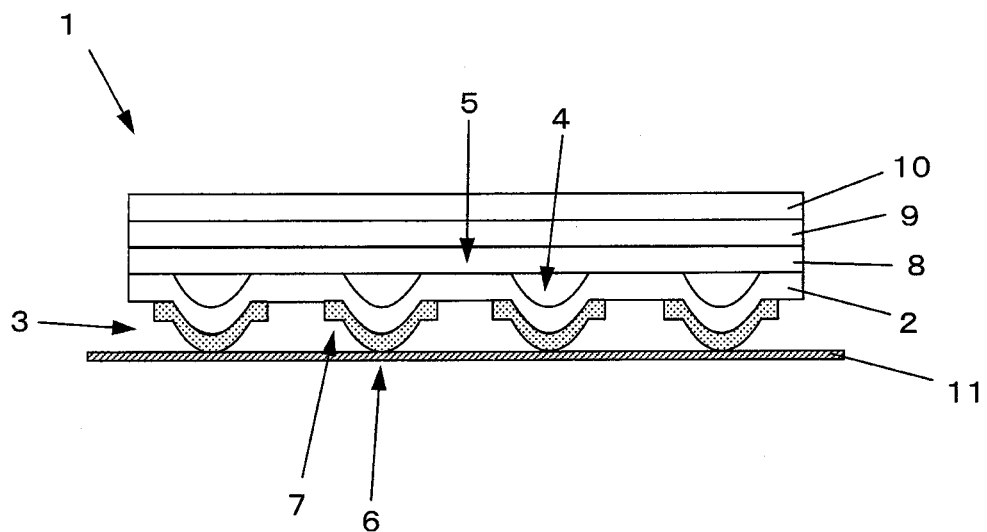
FIG. 3 is a cross-sectional view showing the state of an absorbent article of the disclosure when it has been temporarily positioned.

FIG. 3 is a cross-sectional view showing the state of an absorbent article of the disclosure when it has been temporarily positioned. FIG. 3 corresponds to a cross-section along X-X in FIG. 1. The absorbent article 1 shown in FIG. 3 comprises a top sheet 10, a second sheet 9, a leakproof sheet 8, a back sheet 2 and pressure-sensitive adhesive section 3, which are bonded by a hot-melt adhesive.

In the absorbent article 1 shown in FIG. 3, the protrusions 6 of the pressure-sensitive adhesive section 3 contact with the temporary positioning surface 11 during temporary positioning, while the depressions 7 of the pressure-sensitive adhesive section 3 do not contact with the temporary positioning surface 11. It is therefore easy to peel the absorbent article 1 from the temporary positioning surface 11.

The "temporary positioning surface" may be, for example, clothing, the toilet floor, the inner walls of pipes of a flush toilet, or a toilet bowl, and "temporary positioning" means placement of the absorbent article on the temporary positioning surface by force similar to the weight of the absorbent article itself, including setting, dropping and flushing.

Since the absorbent article of the disclosure can be temporarily positioned on clothing during use, the absorbent article of the disclosure may be placed at a desired location of clothing, and the absorbent article of the disclosure will not readily fall from clothing accidentally until it is placed on the desired location of clothing.

Because the absorbent article of the disclosure has protrusions and depressions formed on the contact surface of the pressure-sensitive adhesive section, it can be easily detached even after it has fallen into a toilet bowl. In addition, even when the unused absorbent article from which the release sheet has been released has been accidentally discarded in a flush toilet, the protrusions and depressions formed on the contact surface of the pressure-sensitive adhesive section render its attachment to the inner walls of pipes more difficult, or allow it to easily detach by a water stream even when it has attached to the inner walls of pipes.

In the absorbent article shown in FIG. 1, a plurality of protruding sections and a continuous depressed section surrounding the protruding sections are formed in the back sheet, and the absorbent article of the disclosure having this construction, even when it has attached to the inner walls of pipes, allows easy infiltration of water between the back sheet of the absorbent article of the disclosure and the inner walls of the pipes, so that the absorbent article of the disclosure is easily detached.

Furthermore, in the absorbent article shown in FIG. 1, the protruding sections of the back sheet are configured in a zigzag fashion, and the absorbent article of the disclosure having such a construction, even when it has attached to the inner walls of pipes, allows easy infiltration of water from any direction between the back sheet of the absorbent article of the disclosure and the inner walls of the pipes, so that the absorbent article of the disclosure is easily detached.

When an absorbent article is used and discarded, the pressure-sensitive adhesive force of the pressure-sensitive adhesive section of the absorbent article is reduced compared to the initial force, and the irregular shape of the fabric of clothing is transferred to the contact surface of the pressure-sensitive adhesive section. Consequently, the problem of attachment to toilet bowls and the inner walls of pipes seldom occurs even when it is discarded in a flush toilet. Furthermore, even when the pressure-sensitive adhesive section of a used absorbent article has attached to the inner walls of pipes, the irregular shape formed in the contact surface of the pressure-sensitive adhesive section allows water to pass between the back sheet and the inner walls of pipes, and especially through the depressions of the pressure-sensitive adhesive section, so that the absorbent article easily detaches from the inner walls of pipes by the water stream and problems, such as clogging seldom occur.

Figure 4:
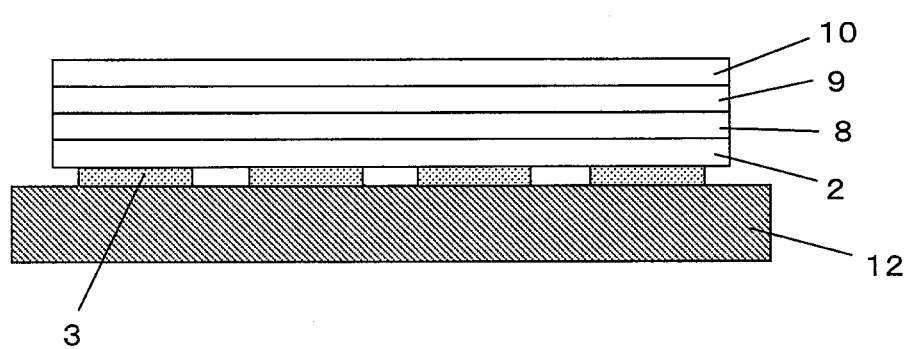
FIG. 4 is a cross-sectional view showing the state of an absorbent article of the disclosure when it is worn by the wearer.

FIG. 4 is a cross-sectional view showing the state of an absorbent article of the disclosure when it is worn by the wearer. FIG. 4 corresponds to a cross-section along X-X in FIG. 1. The absorbent article 1 shown in FIG. 4 comprises a top sheet 10, a second sheet 9, a leakproof sheet 8, a back sheet 2 and pressure-sensitive adhesive section 3, each being bonded by a hot-melt adhesive. The top sheet 10 is also subject to downward body pressure from the body of the wearer, such as the gluteal region.

During wear of the absorbent article 1 shown in FIG. 4, the protruding sections 4 of the back sheet 2 and the depressions 7 of the pressure-sensitive adhesive section 3 collapse under body pressure of the wearer, and the depressions 7 of the pressure-sensitive adhesive section 3 can also contact clothing 12, together with the protrusions 6 of the pressure-sensitive adhesive section 3. Therefore, the pressure-sensitive adhesive section 3 increases the contact area with the clothing 12, and even when the body of the wearer has moved, the absorbent article 1 continues to be attached to the clothing 12.

Body pressure during wear is generally considered to be about 10 g/cm², and when a back sheet, such as shown in FIG. 1 has protruding sections and depressed sections, with protrusions and depressions formed in the pressure-sensitive adhesive section along the protruding sections and depressed sections, the protruding sections of the back sheet preferably collapse under the pressure.

In FIG. 1, the back sheet has protruding sections and depressed sections, with protrusions and depressions formed in the pressure-sensitive adhesive section along the protruding sections and depressed sections, but according to the disclosure, there is no limitation to the embodiment illustrated in FIG. 1 so long as protrusions and depressions are formed on the contact surface of the pressure-sensitive adhesive section.

Figure 5:
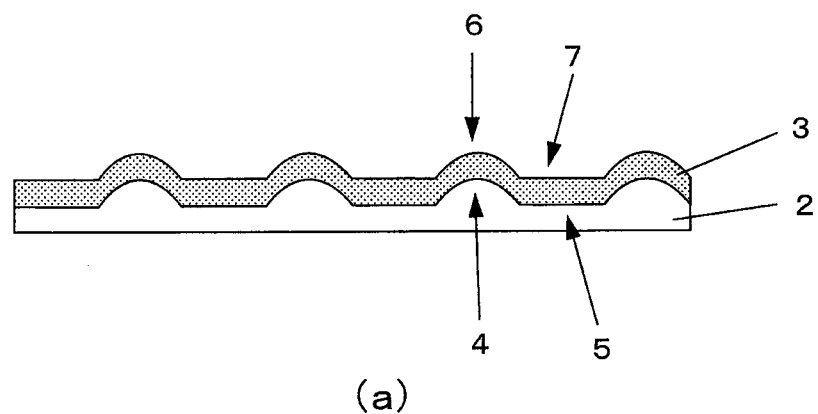
FIG. 5 is an illustration of an example of a back sheet and unevenness on the contact surface of the pressure-sensitive adhesive section.
Figure 5:
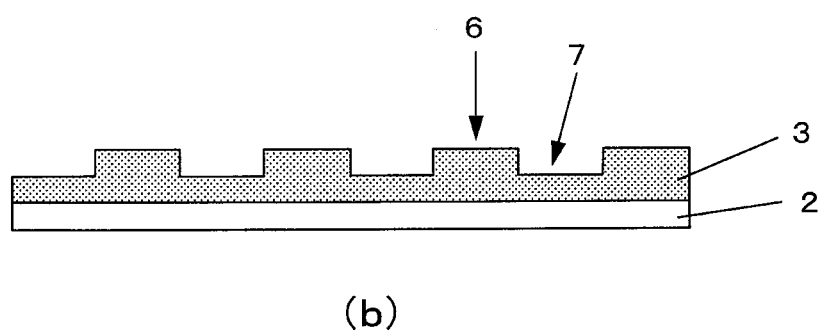

FIG. 5 is an illustration of an example of a back sheet and unevenness on the contact surface of the pressure-sensitive adhesive section. In FIG. 5, elements other than the back sheet and pressure-sensitive adhesive section are omitted.

In the example illustrated in FIG. 5(a), the thickness of the back sheet 2 differs depending on the location, and therefore protruding sections 4 and depressed sections 5 are formed, with protrusions 6 and depressions 7 formed in the pressure-sensitive adhesive section 3 along the protruding sections 4 and depressed sections 5 of the back sheet 2. With the back sheet and pressure-sensitive adhesive section having the shapes shown in FIG. 5(a), the protrusions of the pressure-sensitive adhesive section contact with the temporary positioning surface during temporary positioning, while the depressions of the pressure-sensitive adhesive section do not contact with the temporary positioning surface, whereas during wear, the depressions of the pressure-sensitive adhesive section also contact clothing under body pressure, together with the protrusions of the pressure-sensitive adhesive section.

In the example illustrated in FIG. 5(a), the thickness of the back sheet differs depending on the location, but since the absorbent article of the disclosure and the clothing to which it is attached are both usually soft, the depressions of the pressure-sensitive adhesive section can also contact the clothing under body pressure during wear. Also, the protruding sections of the back sheet may collapse under body pressure.

In the example illustrated in FIG. 5(a), the pressure-sensitive adhesive section 3 has essentially uniform thicknesses, but the pressure-sensitive adhesive section 3 may also differ in thickness depending on the location.

In the example illustrated in FIG. 5(b), the thicknesses of the pressure-sensitive adhesive section 3 differ depending on the location, such that protrusions 6 and depressions 7 are formed in the pressure-sensitive adhesive section 3. With the back sheet and pressure-sensitive adhesive section having the shapes shown in FIG. 5(b), the protrusions of the pressure-sensitive adhesive section contact with the temporary positioning surface during temporary positioning, while the depressions of the pressure-sensitive adhesive section do not contact with the temporary positioning surface, whereas during wear, the depressions of the pressure-sensitive adhesive section also contact clothing under body pressure, together with the protrusions of the pressure-sensitive adhesive section.

In the example illustrated in FIG. 5(b), the thicknesses of the pressure-sensitive adhesive section differ depending on the location, but since the pressure-sensitive adhesive section and the clothing to which they are attached are both usually soft, the depressions of the pressure-sensitive adhesive section can also contact the clothing under body pressure during wear. Also, the protrusions of the pressure-sensitive adhesive section may collapse under body pressure.

In the example illustrated in FIG. 5(b), the back sheet 2 has an essentially uniform thickness, but the back sheet 2 may also differ in thickness depending on the location.

In the embodiment shown in FIG. 5(b), wherein the thicknesses of the pressure-sensitive adhesive section differ depending on the location, such that protrusions and depressions are formed in the pressure-sensitive adhesive section, the protrusions and depressions preferably have the same shapes and configuration as the protruding sections and depressed sections of the back sheet, described below.

In the embodiment shown in FIG. 1, the back sheet contains a mutually independent plurality of protruding sections, and the continuous depressed section surrounding the protruding sections, while the protruding sections of the back sheet are configured in a square zigzag fashion, but according to the disclosure, the shapes and configuration of the protruding sections and depressed sections are not particularly restricted, within a range that exhibits the effect of the disclosure, and it may have protruding sections and depressed sections with various shapes and configurations.

The protruding sections and depressed sections of the back sheet are a means of forming protrusions and depressions in the pressure-sensitive adhesive section, and are an optional element. In the embodiment illustrated in FIG. 5(b), therefore, the back sheet may lack protruding sections and depressed sections.

Figure 6:
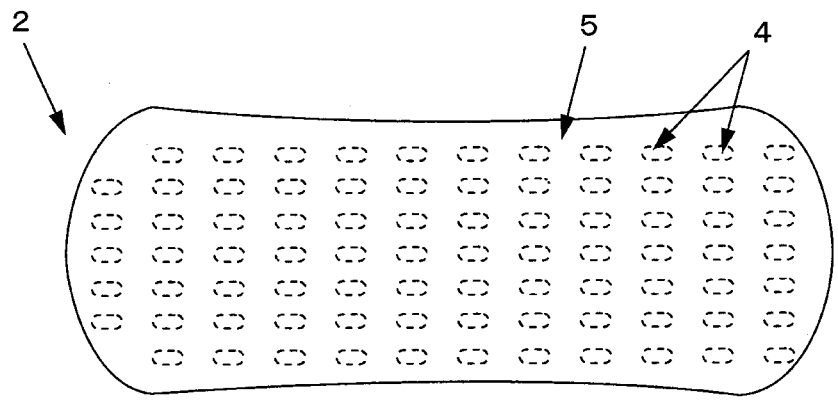
FIG. 6 is an illustration of an example of protruding sections and depressed sections in a back sheet.
Figure 6:
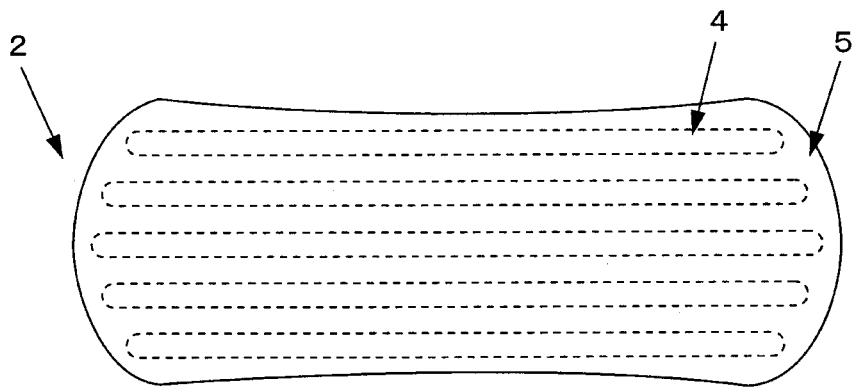
Figure 6:
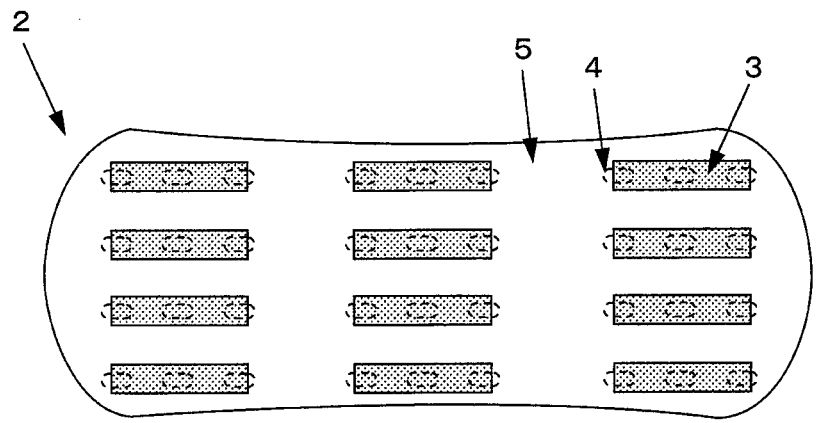

FIG. 6 is an illustration of an example of protruding sections and depressed sections in a back sheet. In FIG. 6(a) and (b), no pressure-sensitive adhesive sections are shown. FIG. 6(a) is an example of a back sheet in which the protruding sections are arranged in series. FIG. 6(b) is an example of a back sheet having protruding sections extending in the lengthwise direction of the absorbent article.

FIG. 6(c) is an example wherein the protruding sections are present only near the regions of the pressure-sensitive adhesive section.

According to the disclosure, the protruding sections of the back sheet are preferably configured in a zigzag fashion, such as a square zigzag or 60° zigzag fashion. When the absorbent article of the disclosure has attached onto the inner wall of a pipe, water can easily infiltrate from any direction between the back sheet and the inner wall of the pipe.

Also according to the disclosure, the length of each of the protruding sections in the lengthwise direction of the absorbent article (hereunder also referred to simply as "length") is preferably about 1 to about 5 times and more preferably about 2 to about 4 times the lengths in the direction perpendicular to the lengthwise direction of the absorbent article (hereunder also referred to simply as "width").

When discarded into a flush toilet, the absorbent article usually flows with the lengthwise direction of the absorbent article parallel to the direction of the water stream, and when the absorbent article clings to the inner wall of a pipe, it usually clings with its lengthwise direction parallel to the direction of the water stream. Consequently, if the lengths of the protruding sections are equal to or greater than the widths of the protruding sections, a greater amount of water will be able to pass between the back sheet and the inner wall of the pipe, when the absorbent article has clung to the inner wall of a pipe, thus allowing the absorbent article to detach more rapidly.

In addition, when the absorbent article has clung with its lengthwise direction parallel to the direction of the water stream, the detachment force during detachment of the absorbent article along the lengthwise direction is proportional to the width of the pressure-sensitive adhesive section in the direction perpendicular to the lengthwise direction, and therefore the lengths of the protruding sections are preferably equal to or greater than the widths of the protruding sections, also for the purpose of reducing the width of the pressure-sensitive adhesive section.

According to the disclosure, the pressure-sensitive adhesive section may be present in a single region over all or a portion of the back sheet, but preferably the pressure-sensitive adhesive section comprises a plurality of mutually independent regions, with protrusions and depressions formed in each of the regions, as shown in FIG. 1.

If the pressure-sensitive adhesive section comprises a plurality of mutually independent regions, the absorbent article of the disclosure, even when it has attached to the inner wall of a pipe, will be able to form channels for passage of a water stream between the back sheet and the inner wall of the pipe, and the absorbent article will be able to detach more rapidly from the inner wall of the pipe.

When the pressure-sensitive adhesive section comprises a plurality of mutually independent regions, as shown in FIG. 1, the area of each of the regions of the pressure-sensitive adhesive section is preferably larger than the area of a protruding section of the back sheet. This will result in formation of a protrusion and a depression in each region.

When the pressure-sensitive adhesive section comprises a plurality of mutually independent regions as shown in FIG. 1, the lengths of the regions of the pressure-sensitive adhesive section in the lengthwise direction of the absorbent article are preferably about 1 to about 5 times and more preferably about 2 to about 4 times their lengths in the direction perpendicular to the lengthwise direction of the absorbent article (hereunder also referred to simply as "width").

As mentioned above, when discarded into a flush toilet, the absorbent article usually flows with the lengthwise direction of the absorbent article parallel to the direction of the water stream, and when the absorbent article clings to a pipe, it usually clings with its lengthwise direction parallel to the direction of the water stream. Consequently, if the lengths of the regions of the pressure-sensitive adhesive section in the lengthwise direction of the absorbent article are equal to or greater than the widths in the direction perpendicular to the lengthwise direction of the absorbent article, a greater amount of water will be able to pass between the back sheet and the inner wall of the pipe, when the absorbent article has clung to the inner wall of a pipe, thus allowing the absorbent article to detach more rapidly.

In addition, when the absorbent article has clung with its lengthwise direction parallel to the direction of the water stream, the detachment force during detachment of the absorbent article along the lengthwise direction is proportional to the width of the pressure-sensitive adhesive section in the direction perpendicular to the lengthwise direction, and therefore in order to weaken the detachment force as well, the lengths of the regions of the pressure-sensitive adhesive section in the lengthwise direction of the absorbent article are preferably equal to or greater than the widths in the direction perpendicular to the lengthwise direction of the absorbent article.

However, the pressure-sensitive adhesive section dissolves and disperses slowly in water, and the pressure-sensitive adhesive section will usually maintain the shape thereof for a while in wastewater treatment tanks. Therefore, if the lengths of the regions of the pressure-sensitive adhesive section are too long, they may become fibrous, clogging and damaging aeration tubes in wastewater treatment tanks. The range specified above is preferred for this reason.

The total area of the pressure-sensitive adhesive section is not particularly restricted so long as the detachment force during detachment of the absorbent article of the disclosure from clothing after wear is no greater than about 5N. However, the area per region, for each of the regions of the pressure-sensitive adhesive section, is preferably no greater than about 900 $mm^2$, more preferably no greater than about 450 $mm^2$, even more preferably no greater than about 250 $mm^2$, and most preferably no greater than about 150 $mm^2$. If large pressure-sensitive adhesive section is floating, it can clog and damage the aeration tubes of wastewater treatment tanks.

The detachment force can be measured in the following manner.

The pressure-sensitive adhesive section side of a back sheet with pressure-sensitive adhesive section is placed over a silk satin glossy surface and sandwiched by acrylic boards and a load of 3.5 kg is applied. After a fixed period of time has elapsed, the detachment force between the back sheet and the silk satin is measured using a Tensilon tester. The initial grip spacing is 20 mm, the pull rate is 300 mm/min, and the maximum load is recorded as the detachment force.

In an embodiment in which the pressure-sensitive adhesive section comprises a plurality of mutually independent regions, as shown in FIG. 1, the back sheet comprises a water disintegratable nonwoven fabric or water disintegratable sheet, and when the water disintegratable nonwoven fabric or water disintegratable sheet is present on the surface of the back sheet that contacts with the pressure-sensitive adhesive section, the spacing between the regions of the pressure-sensitive adhesive section is preferably longer than the fiber lengths of the fibers composing the water disintegratable nonwoven fabric or water disintegratable sheet.

If the pitch of each region of the pressure-sensitive adhesive section is longer than the fiber lengths of the fibers composing the water disintegratable nonwoven fabric or water disintegratable sheet, there will be a lower chance of the regions of the pressure-sensitive adhesive section becoming held while tied by the fibers that were composing the water disintegratable nonwoven fabric or water disintegratable sheet, after the back sheet has water-disintegrated. This will help prevent the regions of the pressure-sensitive adhesive section from becoming tied and fibrous, and becoming entangled in the aeration tubes of wastewater treatment tanks.

The fiber lengths of the fibers composing the water disintegratable nonwoven fabric or water disintegratable sheet is preferably no greater than 8 mm, from the viewpoint of water disintegratability. The regions of the pressure-sensitive adhesive section are therefore preferably more than about 8 mm distant between their perimeters.

In an embodiment in which the water disintegratable nonwoven fabric or water disintegratable sheet is present on the surface of the back sheet that contacts with the pressure-sensitive adhesive section, water can pass through the water disintegratable nonwoven fabric or water disintegratable sheet of the back sheet when the absorbent article of the disclosure has clung to a toilet bowl or the inner wall of a pipe. Thus, when an absorbent article that has clung to a toilet bowl or the inner wall of a pipe has been pressed by a water stream, it escapes the water pressure and the clinging force to inner walls can be reduced. Since water can pass through the water disintegratable nonwoven fabric or water disintegratable sheet and infiltrate between the back sheet and inner wall, the absorbent article of the disclosure readily detaches.

Incidentally, when the back sheet comprises a water disintegratable nonwoven fabric or water disintegratable sheet, the effects of reducing excess buoyancy and of facilitating detachment are further increased.

In the embodiment illustrated in FIG. 1, the pressure-sensitive adhesive section comprises a plurality of mutually independent regions are configured in series on the back sheet, but according to the disclosure, when the pressure-sensitive adhesive section comprises a plurality of mutually independent regions, the regions of the pressure-sensitive adhesive section on the back sheet are not particularly restricted and may be configured in various arrangements.

Figure 7:
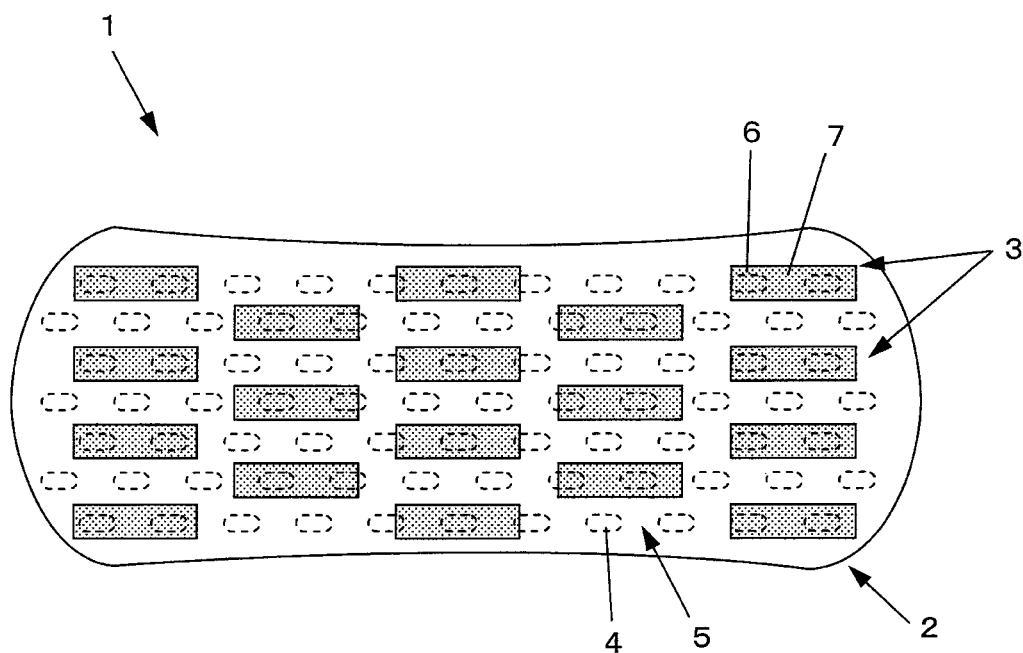
FIG. 7 is an illustration of an example of the configuration of regions of pressure-sensitive adhesive section comprising a plurality of mutually independent regions.

FIG. 7 is an example wherein the regions of the pressure-sensitive adhesive section 3 are configured in a zigzag fashion on the back sheet. By configuring the regions of the pressure-sensitive adhesive section in a zigzag fashion, similar to having the protruding sections of the back sheet configured in a zigzag fashion, the absorbent article of the disclosure allows easy infiltration of water from any direction between the back sheet of the absorbent article of the disclosure and the inner wall of the pipe, when it has attached to the inner wall of a pipe, so that the absorbent article of the disclosure is easily detached.

Examples of back sheets to be used for the disclosure include water disintegratable sheets and water disintegratable nonwoven fabrics that contain water-dispersible fibers. Specifically, there may be mentioned (1) a water disintegratable sheet obtained using pulp as the starting material and forming hydrogen bonds between the pulp fibers to form a sheet, (2) a water disintegratable sheet obtained using water-dispersible fiber, such as pulp or rayon as starting material and forming a sheet with a water-soluble binder, (3) a water disintegratable sheet obtained by tangling water-dispersible fibers to form a sheet, and (4) a water disintegratable nonwoven fabric formed by tangling individual water-dispersible fibers by water jet treatment.

The back sheet may be a layered structure of a water disintegratable sheet or water disintegratable nonwoven fabric containing water-dispersible fibers, and polylactic acid, polyvinyl alcohol or the like.

A specific example of a back sheet to be used for the disclosure is water disintegratable wet spunlace.

The top sheet to be used for the disclosure is not particularly restricted so long as it is one used as a water disintegratable top sheet in the technical field, and for example, it may be the same type of water disintegratable nonwoven fabric or water disintegratable sheet mentioned above for the back sheet.

The pressure-sensitive adhesive section used for the disclosure may employ a pressure-sensitive adhesive commonly used in the technical field, such as a hot-melt pressure-sensitive adhesive, which may be a polyolefinic (for example, polyethylene or polypropylene) hot-melt pressure-sensitive adhesive, an ethylene/vinyl acetate copolymer-based hot-melt pressure-sensitive adhesive, synthetic rubber-based (for example, styrene-based copolymer, butadiene-based copolymer or isoprene-based copolymer) hot-melt pressure-sensitive adhesive, an acrylic resin-based pressure-sensitive adhesive, or a polyvinyl alcohol-based pressure-sensitive adhesive.

The pressure-sensitive adhesive may also be an acrylic emulsion having a hydrophilic protective colloid layer.

The release sheet to be used for the disclosure may have the surface of a water disintegratable sheet, such as a water disintegratable sheet coated with a water disintegratable resin, such as polyvinyl alcohol, with the surface coated with a silicone resin.

The second sheet to be optionally used for the disclosure is not particularly restricted so long as it is one used as a water disintegratable second sheet in the technical field, and for example, it may be the same type of water disintegratable nonwoven fabric or water disintegratable sheet mentioned above for the back sheet.

The leakproof sheet to be optionally used for the disclosure is not particularly restricted so long as it is one used as a water disintegratable leakproof sheet in the technical field, and for example, it may be the same type of water disintegratable nonwoven fabric or water disintegratable sheet mentioned above for the back sheet, with a layered structure comprising a water disintegratable sheet, water disintegratable nonwoven fabric or the like and polylactic acid or polyvinyl alcohol.

The leakproof sheet may also be a film made of polylactic acid, polyvinyl alcohol or the like.

A specific example of a leakproof sheet to be used for the disclosure is a layered structure comprising water disintegratable wet spunlace and polylactic acid.

A method for producing the absorbent article of the disclosure will now described.

A first embodiment of the method for producing an absorbent article according to the disclosure comprises a step of layering the back sheet, pressure-sensitive adhesive section and release sheet with the pressure-sensitive adhesive section inserted between them to form a layered structure, a step of shaping the layered structure so that the contact surface of the pressure-sensitive adhesive section has unevenness, to form a shaped layered structure, and a step of layering the top sheet on the shaped layered structure.

As an example of the step of layering the back sheet, pressure-sensitive adhesive section and release sheet with the pressure-sensitive adhesive section inserted between them to form a layered structure, there may be mentioned (i) a step in which the pressure-sensitive adhesive section is coated onto the back sheet and then the release sheet is attached thereover to form a layered structure, and (ii) a step in which the pressure-sensitive adhesive section is coated onto the release sheet and then the back sheet is attached thereover to form a layered structure.

Figure 8:
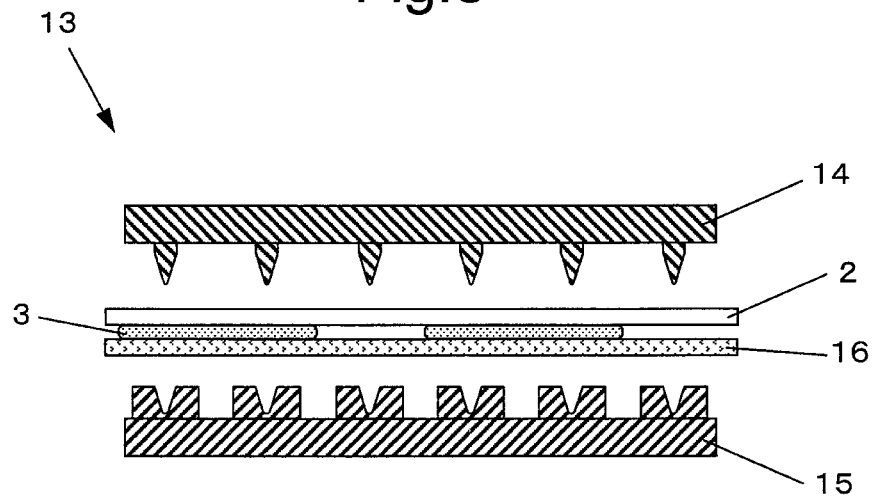
FIG. 8 is a diagram for illustration of embossing.

The step of shaping the layered structure so that the contact surface of the pressure-sensitive adhesive section has unevenness, in order to form a shaped layered structure, may be a step of embossing the layered structure. As an example of embossing, any means known in the art may be employed, such as the one described in Japanese Unexamined Patent Publication No. 2009-273722, and for example, embossing may be accomplished using an embossing pattern 13 with a protrusion pattern 14 and depression pattern 15, such as illustrated in FIG. 8. The layered structure comprising the back sheet 2, pressure-sensitive adhesive section 3 and release sheet 16 are placed between the protrusion pattern 14 and depression pattern 15 of the embossing pattern 13, and the layered structure is pressed by the protrusion pattern 14 and depression pattern 15 to form a shaped layered structure. The temperature for pressing will usually be between about 50° C. and 60° C.

Also, only one side of the release sheet may be shaped by embossing or the like to form unevenness on the contact surface of the pressure-sensitive adhesive section.

The step of layering the top sheet on the shaped layered structure may be one in which the shaped layered structure and the top sheet are attached with a hot-melt adhesive or the like inserted between them. When the absorbent article comprises an optional sheet, such as a second sheet or leakproof sheet, the stack of the top sheet, second sheet, leakproof sheet or the like attached with a hot-melt adhesive inserted between them may be attached to the aforementioned shaped layered structure.

Next, the layered structure comprising the top sheet may be cut into the shape of the absorbent article.

A second embodiment of the method for producing an absorbent article according to the disclosure may comprise a step of layering the top sheet, back sheet, pressure-sensitive adhesive section and release sheet with the pressure-sensitive adhesive section disposed between the back sheet and the release sheet, to form a layered structure, a step of shaping the layered structure so that the contact surface of the pressure-sensitive adhesive section has unevenness.

As examples of a step of layering the top sheet, back sheet, pressure-sensitive adhesive section and release sheet with the pressure-sensitive adhesive section disposed between the back sheet and release sheet, to form a layered structure, there may be mentioned (i) a step in which the pressure-sensitive adhesive section is coated onto the back sheet and then the release sheet is attached thereover and the back sheet and top sheet are attached in any desired order with a hot-melt adhesive or the like inserted between them, to form a layered structure, and (ii) a step in which the pressure-sensitive adhesive section is coated onto the release sheet and then the back sheet is attached thereover and the back sheet and top sheet are attached in any desired order with a hot-melt adhesive or the like inserted between them, to form a layered structure. When the absorbent article comprises an optional sheet, such as a second sheet or leakproof sheet, the stack of the top sheet, second sheet, leakproof sheet or the like attached with a hot-melt adhesive inserted between them may be attached to the back sheet in any desired order.

The step of shaping the layered structure so that the contact surface of the pressure-sensitive adhesive section has unevenness may be a step of embossing the layered structure. As an example of embossing, any means known in the art may be employed, such as embossing accomplished using an embossing pattern 13 with a protrusion pattern 14 and depression pattern 15, such as illustrated in FIG. 8.

Also, only one side of the release sheet may be shaped by embossing or the like to form unevenness on the contact surface of the pressure-sensitive adhesive section.

Next, the shaped layered structure may be cut into the shape of the absorbent article.

In the second embodiment of the method of producing an absorbent article according to the disclosure, the top sheet is subjected to shaping treatment together with the back sheet, the pressure-sensitive adhesive section and the release sheet. Since the top sheet will thus have unevenness, absorption of body fluids during wear will be improved, clinging to skin during wear will be reduced, and clinging of the top sheet side of the absorbent article to toilet bowls and pipes after disposal of the top sheet will be reduced.

For production of an absorbent article comprising a back sheet, such as shown in FIG. 5(*a*), a back sheet, such as shown in FIG. 5(*a*) may be prepared and, as mentioned above, each sheet may be attached using a hot-melt adhesive or the like.

For production of an absorbent article comprising pressure-sensitive adhesive section as shown in FIG. 5(*b*), (i) the pressure-sensitive adhesive section may be coated non-uniformly on the back sheet as shown in FIG. 5(*b*), and as mentioned above, each sheet may be attached using a hot-melt adhesive or the like, or (ii) the pressure-sensitive adhesive section may be coated to uniform thickness on the back sheet, and a release sheet coated with the pressure-sensitive adhesive section in a fixed pattern, such as in a dot-like zigzag fashion, may be attached to a back sheet having pressure-sensitive adhesive section of uniform thickness, and then another sheet attached to this stack.

EXAMPLES

The disclosure will now be explained in greater detail using examples and comparative examples, with the understanding that the disclosure is in no way limited by the examples.

Example 1

The panty liner 1 shown in FIG. 1 was prepared (length in lengthwise direction of product: 140 mm, product width: 56 mm). The regions of the pressure-sensitive adhesive section had sizes of approximately 25 mm×8 mm, and were configured with spacings of approximately 25 mm in the lengthwise direction and approximately 9 mm in the widthwise direction. Also, the panty liner 1 had the top sheet, back sheet, pressure-sensitive adhesive section and release sheet integrally shaped, with protrusions and depressions formed as shown in FIG. 1.

Water was poured on a vinyl chloride sheet tilted 30°, and the panty liner 1 (a total of 3 sheets) was placed thereover and allowed to naturally drop from a height of about 1 m while being attached by its own weight. Next, tap water (approximately 2 L) was allowed to flow for about 1 minute from about 20 cm above the panty liner 1 along the vinyl chloride sheet. When water was poured 10 times in the lengthwise direction of the panty liner 1, and then 10 times in the widthwise direction of the panty liner 1 by rotating the vinyl chloride sheet, all three sheets were separated from the vinyl chloride sheet.

Comparative Example 1

There were prepared the panty liner 1 used in Example 1 and a panty liner 2 which was identical except for not being shaped, and the same test was conducted as in Example 1. As a result, one of the three sheets remained attached to the vinyl chloride sheet.

Reference Signs List
1 Absorbent article
2 Back sheet
3 Pressure-sensitive adhesive section
4 Protruding section
5 Depressed section
6 Protrusion
7 Depression
8 Leakproof sheet
9 Second sheet
10 Top sheet
11 Temporary positioning surface
12 Clothing
13 Embossing pattern
14 Protrusion pattern
15 Depression pattern
16 Release sheet

The invention claimed is:

1. An absorbent article having water disintegratability comprising:
a water disintegratable to sheet,
a water disintegratable back sheet,
a pressure-sensitive adhesive section for attaching the absorbent article to clothing, disposed on the surface of the back sheet opposite the to sheet, and
a release sheet for protection of a contact surface of the pressure-sensitive adhesive section which contacts with clothing,
wherein one or more protrusions and one or more depressions are formed on the contact su r face of the pressure-sensitive adhesive section,
wherein the back sheet has one or more protruding sections and one or more depressed sections, and the protrusions and depressions of the pressure-sensitive adhesive section are formed along the protruding sections and depressed sections, respectively, and
wherein the pressure-sensitive adhesive section comprises a plurality of mutually independent regions, and the protrusions and depressions are formed in each of the regions.

2. The absorbent article according to claim 1, wherein the back sheet comprises a water disintegratable nonwoven fabric or a water disintegratable sheet, and the water disintegratable nonwoven fabric or water disintegratable sheet is present on the surface of the back sheet that contacts with the pressure-sensitive adhesive section.

3. The absorbent article according to claim 2, wherein a spacing between the regions of the pressure-sensitive adhesive section is longer than fiber lengths of fibers composing the water disintegratable nonwoven fabric or water disintegratable sheet.

4. The absorbent article according to claim 1, wherein the area of each of the regions of the pressure-sensitive adhesive section is larger than the area of each of the protruding sections of the back sheet.

5. The absorbent article according to claim 1, wherein a length of each of the regions of the pressure-sensitive adhesive section in a lengthwise direction of the absorbent article is longer than a length in the direction perpendicular to a lengthwise direction of the absorbent article.

6. An absorbent article having water disintegratability comprising:
a water disintegratable top sheet,
a water disintegratable back sheet,
a pressure-sensitive adhesive section for attaching the absorbent article to clothing, disposed on the surface of the back sheet opposite the top sheet, and
a release sheet for protection of a contact surface of the pressure-sensitive adhesive section which contacts with clothing,
wherein the back sheet has a plurality of protruding sections configured in a zigzag fashion and a continuous depressed section surrounding the protruding sections, and one or more protrusions and one or more depressions are formed on the contact surface of the pressure-sensitive adhesive section, along the protruding sections and depressed sections, respectively,
the pressure-sensitive adhesive section comprises a plurality of mutually independent regions, and the protrusions and depressions are formed in each of the regions, the back sheet comprises a water disintegratable nonwoven fabric or water disintegratable sheet, the area of each of the regions of the pressure-sensitive adhesive section in which the water disintegratable nonwoven fabric or water disintegratable sheet is present, on the surface of the back sheet which contacts with the pressure-sensitive adhesive section, is larger than the area of each of the protruding sections of the back sheet, a length of each of the regions of the pressure-sensitive adhesive section in a lengthwise direction of the absorbent article is longer than its length in a direction perpendicular to the lengthwise direction of the absorbent article, and a spacing between the regions of the pressure-sensitive adhesive section is longer than fiber lengths of fibers composing the water disintegratable nonwoven fabric or water disintegratable sheet, and
the protrusions and depressions are formed on the contact surface of the pressure-sensitive adhesive section by integrally shaping the top sheet, back sheet, pressure-sensitive adhesive section and release sheet.

7. An absorbent article having water disintegratability comprising:
a water disintegratable to sheet,
a water disintegratable back sheet,
a pressure-sensitive adhesive section for attaching the absorbent article to clothing, disposed on the surface of the back sheet opposite the to sheet, and
a release sheet for protection of a contact surface of the pressure-sensitive adhesive section which contacts with clothing,
wherein one or more protrusions and one or more depressions are formed on the contact surface of the pressure-sensitive adhesive section, and
wherein the pressure-sensitive adhesive section has different thicknesses at the protrusions and depressions, whereby the protrusions and depressions are formed on the contact surface of the pressure-sensitive adhesive section.

8. An absorbent article having water disintegratability comprising:
a water disintegratable to sheet,
a water disintegratable back sheet,
a pressure-sensitive adhesive section for attaching the absorbent article to clothing, disposed on the surface of the back sheet opposite the to sheet, and
a release sheet for protection of a contact surface of the pressure-sensitive adhesive section which contacts with clothing,
wherein one or more protrusions and one or more depressions are formed on the contact su r face of the pressure-sensitive adhesive section,
wherein the back sheet has one or more protruding sections and one or more depressed sections, and the protrusions and depressions of the pressure-sensitive adhesive section are formed along the protruding sections and depressed sections, respectively, wherein the back sheet comprises a plurality of mutually independent protruding sections and a continuous depressed section surrounding the protruding sections, and wherein the pressure-sensitive adhesive section comprises a plurality of mutually independent regions, and the protrusions and depressions are formed in each of the regions.

9. The absorbent article according to claim 8, wherein the back sheet comprises a water disintegratable nonwoven fabric or a water disintegratable sheet, and the water disintegratable nonwoven fabric or water disintegratable sheet is present on the surface of the back sheet that contacts with the pressure-sensitive adhesive section.

10. The absorbent article according to claim 8, wherein the area of each of the regions of the pressure-sensitive adhesive section is larger than the area of each of the protruding sections of the back sheet.

11. An absorbent article having water disintegratability comprising:
- a water disintegratable to sheet,
- a water disintegratable back sheet,
- a pressure-sensitive adhesive section for attaching the absorbent article to clothing, disposed on the surface of the back sheet opposite the to sheet, and
- a release sheet for protection of a contact surface of the pressure-sensitive adhesive section which contacts with clothing, wherein one or more protrusions and one or more depressions are formed on the contact surface of the pressure-sensitive adhesive section, wherein the back sheet has one or more protruding sections and one or more depressed sections, and the protrusions and depressions of the pressure-sensitive adhesive section are formed along the protruding sections and depressed sections, respectively, wherein the back sheet comprises a plurality of mutually independent protruding sections and a continuous depressed section surrounding the protruding sections, wherein the protruding sections of the back sheet are configured in a zigzag fashion, and wherein the pressure-sensitive adhesive section comprises a plurality of mutually independent regions, and the protrusions and depressions are formed in each of the regions.

12. The absorbent article according to claim 11, wherein the back sheet comprises a water disintegratable nonwoven fabric or a water disintegratable sheet, and the water disintegratable nonwoven fabric or water disintegratable sheet is present on the surface of the back sheet that contacts with the pressure-sensitive adhesive section.

* * * * *